United States Patent [19]
Krishnamurti et al.

[11] Patent Number: 5,637,659
[45] Date of Patent: Jun. 10, 1997

[54] METHOD OF POLYMERIZING OLEFINS USING BORABENZENE CATALYSTS

[75] Inventors: Ramesh Krishnamurti, Amherst; Sandor Nagy, Grand Island, both of N.Y.; Bradley P. Etherton, Houston, Tex.

[73] Assignee: Lyondell Petrochemical Company, Houston, Tex.

[21] Appl. No.: 651,190

[22] Filed: May 17, 1996

Related U.S. Application Data

[62] Division of Ser. No. 373,814, Jan. 17, 1995, Pat. No. 5,554,775.
[51] Int. Cl.⁶ .................................................. C08F 4/64
[52] U.S. Cl. .......................... 526/133; 526/132; 526/160; 526/161; 526/280; 526/281; 526/348.2; 526/348.4; 526/348.5; 526/348.6; 526/348.7; 526/352; 526/943; 502/117; 502/155
[58] Field of Search .................................. 526/132, 133, 526/160, 161, 280, 281, 348.2, 348.4, 348.5, 348.6, 348.7, 352, 943

[56] References Cited

U.S. PATENT DOCUMENTS 5,457,171 10/1995 Langhauser et al. ............... 526/132
5,468,889 11/1995 Srebnik et al. ....................... 556/7

OTHER PUBLICATIONS

Article: "Borabenzene Derivatives. 21.[1] 2,4–Penta-Dienylboranes as Key Intermediates of a Novel Route to Boracyclohexadienes and Boratabenzenes," Structure of [Li(TMPDA)] ($C_5H_5BNMe_2$), by Gerhard E. Herberich et al., Organometallics, 1993, pp. 2891–2893.
Structure of [Li(TMPOA)] ($C_5H_5BNMe_2$), by Gerhard E. Herberich et al., Organometallics, 1993, pp. 2891–2893.

*Primary Examiner*—David W. Wu
*Attorney, Agent, or Firm*—Liddell, Sapp, Zivley, Hill & LaBoon, L.L.P.

[57] ABSTRACT

Disclosed is a catalyst having the general formula

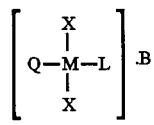

where Q is a ligand containing the ring

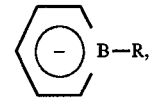

R is hydrogen, $N(R')_2$, $OR'$, or $R'$, each $R'$ is independently selected from alkyl from $C_1$ to $C_{10}$, aryl from $C_6$ to $C_{15}$, alkaryl $C_7$ to $C_{15}$, and aralkyl from $C_7$ to $C_{15}$, each X is independently selected from hydrogen, halogen, alkoxy from $C_1$ to $C_{10}$, dialkylamino from $C_1$ to $C_{10}$, methyl,

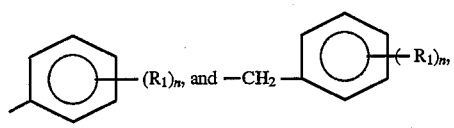

each $R_1$ is independently selected from halogen, alkoxy from $C_1$ to $C_{10}$, and $R'$, L is

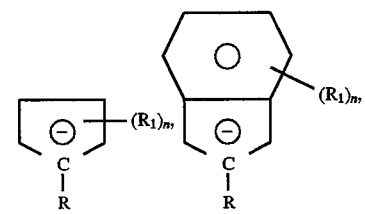

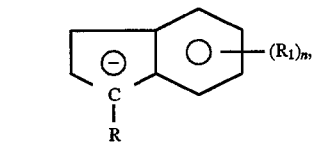

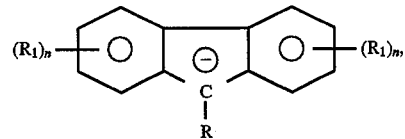

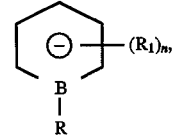

Q, or X, where L can be bridged to Q, B is an optional base, "n" is 0 to 5, and M is titanium, zirconium, or hafnium.

25 Claims, No Drawings

METHOD OF POLYMERIZING OLEFINS USING BORABENZENE CATALYSTS

This application is a division of application Ser. No. 08/373,814, filed Jan. 17, 1995 now U.S. Pat. No. 5,554,775.

BACKGROUND OF THE INVENTION

This invention relates to catalysts useful in homo- and co-polymerizing ethylene and other olefinic hydrocarbons. In particular, it relates to catalysts containing a transition metal π-bonded to a ligand that contains a borabenzene ring.

Until recently, polyolefins have been primarily made with conventional Ziegler catalyst systems. These catalysts typically consist of transition metal-containing compounds and one or more organometallic compound. For example, polyethylene has been made using Ziegler catalysts such as titanium trichloride and diethylaluminum chloride, or a mixture of titanium tetrachloride, vanadium oxytrichloride, and triethylaluminum. These catalysts are inexpensive but they have low activity and therefore must be used at high concentrations. As a result, it is sometimes necessary to remove catalyst residues from the polymer, which adds to production costs. Neutralizing agents and stabilizers must be added to the polymer to overcome the deleterious effects of the catalyst residues. Failure to remove catalyst residues leads to polymers having a yellow or grey color and poor ultraviolet and long term stability. For example, chloride-containing residues can cause corrosion in polymer processing equipment. Furthermore, Ziegler catalysts produce polymers having a broad molecular weight distribution, which is undesirable for some applications such as injection molding. They are also poor at incorporating α-olefin co-monomers. Poor co-monomer incorporation makes it difficult to control the polymer density. Large quantities of excess co-monomer may be required to achieve a certain density and many higher α-olefins, such as 1-octene, may be incorporated at only very low levels, if at all.

Although substantial improvements in Ziegler catalyst systems have occurred since their discovery, these catalysts are now being replaced with the recently discovered metallocene catalyst systems. A metallocene catalyst typically consists of a transition metal compound which has one or more cyclopentadienyl ring ligands. They have low activities when used with organometallic compounds, such as aluminum alkyls, which are used with traditional Ziegler catalysts, but very high activities when used with aluminoxanes as cocatalysts. The activities are generally so high that catalyst residues need not be removed from the polymer. Furthermore, they produce polymers with high molecular weights and narrow molecular weight distributions. They also incorporate α-olefin co-monomers well. However, at higher temperatures metallocene catalysts tend to produce lower molecular weight polymers. Thus, they are useful for gas phase and slurry polymerizations of ethylene, which are conducted at about 80° C. to about 95° C., but they do not generally work well in solution polymerizations of ethylene, at about 150° C. to about 250° C. The polymerization of ethylene in solution is desirable because it allows great flexibility for producing polymers over a wide range of molecular weights and densities as well as the use of a large variety of different co-monomers. One can produce polymers that are useful in many different applications. For example, high molecular weight, high density polyethylene (PE) film useful as a barrier film for food packaging and low density ethylene co-polymers with good toughness and high impact strength.

SUMMARY OF THE INVENTION

We have found a new class of catalysts based on a bora-benzene ring structure and containing a transition metal. The catalysts of this invention have unusually high activities, which means that they can be used in very small quantities. They are also very good at incorporating co-monomers into the polymer. They have good activity at higher temperatures and are therefore expected to be useful in solution polymerizations of ethylene. Finally, some of the catalysts within the scope of this invention contain tertiary amine groups. It is surprising that these catalysts are effective because many amine-containing compounds are known to be catalyst poisons.

DESCRIPTION OF THE PREFERRED EMBODIMENTS

The catalysts of this invention have the general formula

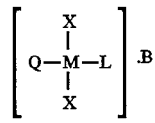

In the formula, Q is a ligand containing a bora-benzene ring. A bora-benzene ring has the structure

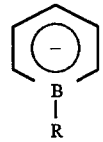

where R can be hydrogen, $N(R')_2$, $OR'$, or $R'$, where each $R'$ is independently selected from alkyl from $C_1$ to $C_{10}$, aryl from $C_6$ to $C_{15}$, alkaryl from $C_7$ to $C_{15}$, and aralkyl from $C_7$ to $C_{15}$. The R group is preferably $—N(R')_2$ or phenyl, as those catalysts have the best properties and, if R is $—N(R')_2$, then the R' in $—N(R')_2$ is preferably methyl. Examples of Q ligands include

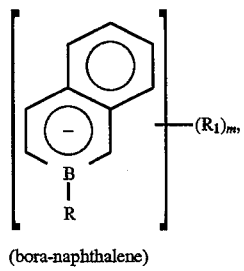

(bora-naphthalene)

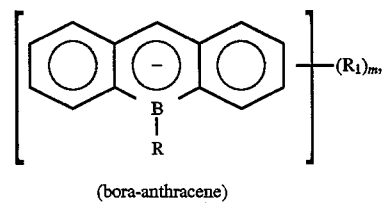

(bora-anthracene)

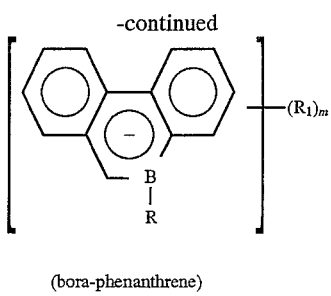

(bora-phenanthrene)

where "m" is 0 to the maximum number of substitutable positions, and is preferably 0 as those catalysts are easier to make. Each $R_1$ is independently selected from halogen, alkoxy from $C_1$ to $C_{10}$, and R'. The preferred Q ligands are bora-benzene, bora-naphthalene, and bora-anthracene because those catalysts are easier to prepare.

In the general formula, each X is independently selected from hydrogen, halogen, alkoxy from $C_1$ to $C_{10}$, dialkylamino from $C_1$ to $C_{10}$, methyl,

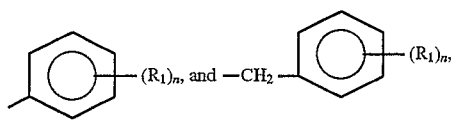

where "n" is 0 to 5 and preferably is 0. The X group is preferably chlorine or methyl, as those catalysts are easy to prepare and have good properties.

Also, L in the general formula can be

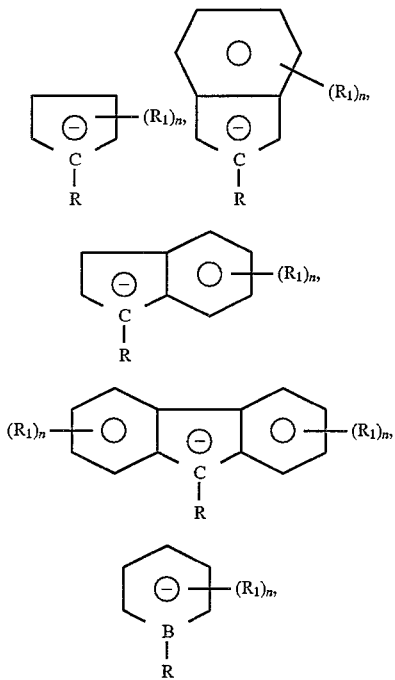

Q, or X. Preferably, L is Q, cyclopentadienyl, or chlorine because those catalysts are easiest to prepare and have good properties.

Optionally, L can be bridged to Q. Groups that can be used to bridge two ligands include methylene, ethylene, 1,2-phenylene, dimethyl silyl, diphenyl silyl, diethyl silyl, and methyl phenyl silyl. Normally, only a single bridge is used in a catalyst. It is believed that bridging the ligand changes the geometry around the catalytically active transition metal and improves catalyst activity and other properties, such as comonomer incorporation and thermal stability.

The M group in the general formula can be titanium, zirconium, or hafnium, but is preferably zirconium as those catalysts have a good combination of high activity and good stability.

In the general formula, B is an optional Lewis base. Up to an equimolar amount (with M) of base can be used. The use of a Lewis base is generally not preferred because it tends to decrease catalyst activity. However, it also tends to improve catalyst stability, so its inclusion may be desirable, depending upon the process in which it is being used. The base can be residual solvent from the preparation of the catalyst, or it can be added separately in order to enhance properties of the catalyst. Examples of bases that can be used in this invention include ethers such as diethyl ether, dibutyl ether, tetrahydrofuran, and 1,2-dimethoxyethane, esters such as n-butyl phthalate, ethyl benzoate, and ethyl p-anisate, and phosphines such as triethylphosphine, tributylphosphine, and triphenylphosphine.

Preparation of the Q ligand portion of the catalyst can be found in the literature. See, for example, "Borabenzene Derivatives 21. 2,4-Pentadienylboranes as Key Intermediates of a Novel Route to Boracyclohexadienes and Boratabenzenes. Structure of [Li(TMEDA)]($C_5H_5BNMe_2$)" by Gerhard E. Herberich et al., *Organometallics* (1993), pages 2891–2893, herein incorporated by reference. In that article, 2,4-pentadienylborane is reacted with a lithium amide in tetrahydrofuran in the presence of tetramethylethylenediamine (TMEDA) to form a dimethylamino borabenzenyl lithium TMEDA complex having the formula

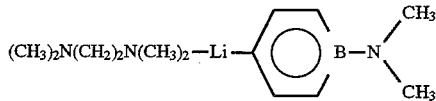

See also, "Reactions of the 9-Mesityl-9-boraanthracene Anion" by R. Van Veen and F. Bickelhaupt, *Journal of Organometallic Chemistry*, (1974), pages 153–165, which describes the formation of 9-mesityl-9-boraanthracenyllithium.

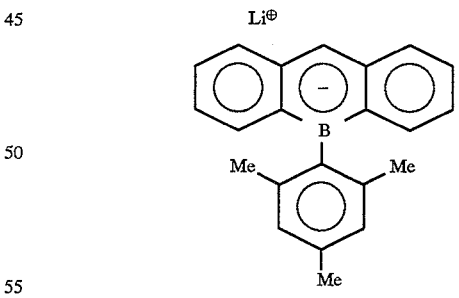

Other Q ligands can be prepared in an analogous manner or by other processes. The catalyst can be made from the Q ligand by adding a suspension of an appropriate tetravalent metal compound to a solution of the Q ligand. This reaction can occur at about −78° C. to about 50° C., but is preferably performed below 0° C.

Since the catalyst is normally used in conjunction with an organometallic co-catalyst, it is preferable to dissolve the catalyst in a solvent in which the co-catalyst is also soluble. For example, if methylaluminoxane (MAO) or polymethylaluminoxane (PMAO) is the co-catalyst, then toluene, xylene, benzene, or ethylbenzene could be used as the solvent. Other suitable co-catalysts include aluminum alkyls having the formula $AlR'_{x(R2)3-x}$, where $1 \leq X \leq 3$ and $R_2$ is hydrogen, halide, or alkyl or alkoxide from $C_1$ to $C_{20}$, such as triethylaluminum and ethylaluminum dichloride. The preferred co-catalyst is MAO as it results in high activity and a polymer having a narrower molecular weight distribution. The mole ratio of the organometallic cocatalyst to catalyst when used in a polymerization is generally in the range 0.01:1 to 100,000:1, and preferably ranges from 1:1 to 10,000:1.

To enhance its properties, the catalyst can be used with an acid salt that contains a non-coordinating inert anion (see U.S. Pat. No. 5,064,802). The acid salt is generally a non-nucleophilic compound that consists of bulky ligands attached to a boron or aluminum atom, such as lithium tetrakis(pentafluorophenyl) borate, lithium tetrakis (pentafluorophenyl)aluminate, anilinium tetrakis (pentafluorophenyl)borate, and mixtures thereof. The anion which results when these compounds react with the catalyst is believed to be weakly coordinated to the metal-containing cation. The mole ratio of acid salt to catalyst can range from about 0.01:1 to about 1000:1, but is preferably about 1:1 to 10:1. While there is no limitation on the method of preparing an active catalyst system from the catalyst and the acid salt, preferably they are mixed in an inert solvent at temperatures in the range of about −78° C. to about 150° C. They can also be mixed in the presence of monomer if desired. The acid salt can be used in combination with the organometallic cocatalysts described earlier.

The catalyst and co-catalyst can be used on a support such as silica gel, alumina, silica, magnesia, or titania, but supports are not preferred as they may leave contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. In order to use a support, the catalyst and co-catalyst are dissolved in the solvent and are precipitated onto the support material by, for example, the evaporation of solvent. The co-catalyst can also be deposited on the support or it can be introduced into the reactor separately from the supported catalyst.

Once the catalyst has been prepared it should be used as promptly as possible as it may lose some activity during storage. Storage of the catalyst should be at a low temperature, such as −100° C. to about 20° C. The catalyst is used in a conventional manner in the polymerization of olefinic hydrocarbon monomers. While unsaturated monomers such as styrene can be polymerized using the catalysts of this invention, it is particularly useful for polymerizing α-olefins such as propylene, 1-butylene, 1-hexene, 1-octene, and especially ethylene.

The catalyst is also useful for copolymerizing mixtures of ethylene with unsaturated monomers such as 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbornene, ethylidene norbornene, vinyl norbornene, and the like.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −100° C. to about 300° C. The catalyst can be used in a conventional manner in the co-polymerization of olefin monomers such as ethylene, propylene, 1-butene, 1-octene, 1-hexene, norbornene, and norbornadiene.

The following examples further illustrate this invention.

EXAMPLE 1

This example describes the synthesis of (B-dimethylamino-borabenzene) cyclopentadienylzirconium dichloride, which has the formula

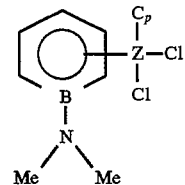

where Cp is cyclopentadienyl and Me is methyl.

To a suspension of 0.56 grams (2.13 mmole) of cyclopentadienylzirconium trichloride (purchased from Strem Chemicals) in 15 ml of absolute ether, a solution of 0.61 g (2.51 mmole) of dimethylamino borabenzenyl lithium tetramethylethylenediamine complex, (prepared according to the hereinabove cited article by G. E. Herberich) in 10 ml of ether was added at −78° C. The mixture was warmed to room temperature and was stirred for an additional 1 hour. After the volatiles had been removed in vacuo, the residue was washed with 30 ml of hexane and extracted with 30 ml of toluene. The toluene was evaporated under reduced pressure to give 0.23 grams of a black solid. Proton NMR spectrum indicated the presence of some impurities in the product.

EXAMPLE 2

This example describes the synthesis of cyclopentadienyl (9-mesitylboraanthracenyl) zirconium dichloride, which has the formula

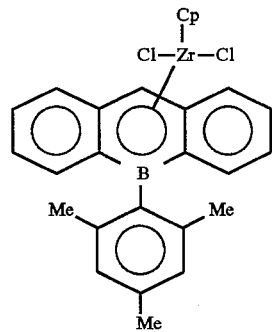

A solution of 9-mesitylboraanthracenyllithium in diethyl ether was prepared by adding 1.0 mL of 1.6M n-butyllithium in hexanes to a solution of 0.47 g (1.6 mmol) of 9-mesitylboraanthracene in 18 mL diethyl ether at −78° C., warming to room temperature, and stirring for an additional 2 hours. The solution was cooled to −10° C. and 0.42 g (1.6 mmol) of cyclopentadienylzirconium trichloride (Strem Chemicals) was added. The bath was then allowed to reach room tmperature, and the reaction mixture was stirred overnight. The volatiles were removed in vacuo to give a reddish brown powder. To this was added 20 mL dry toluene and the mixture ws filtered to give a clear yellow-orange filtrate which was concentrated to give a brown foam. This was treated with dry hexane (20 mL) and the mixture filtered to give 0.26 g of a light tan solid. Proton NMR spectrum of the product indicated the presence of some impurities.

EXAMPLES 3 TO 17

Ethylene was polymerized using the catalysts of Examples 1 and 2. (Examples 3 through 13 and Example 20 used the catalyst prepared in Example 1 and Examples 14 through 19 used the catalyst prepared in Example 2.) The polymerizations were conducted in a stirred 1.7 liter autoclave at 80° or 110° C. Dry, oxygen-free toluene (840 ml) was charged to a clean, dry, oxygen-free reactor. MAO from Ethyl Corporation (10 wt. % in toluene) was used in some of the polymerizations. Other polymerizations were conducted using PMAO from Akzo Chemical (25 wt. % in toluene). The desired amount of MAO or PMAO to give the ratio shown in the table which follows was added by syringe at 30° C. The reactor was heated to the desired temperature and sufficient ethylene was added to bring the reactor pressure to 150 psig. The reactor was allowed to equilibrate at the desired temperature and pressure. A solution of catalyst was prepared by dissolving 0.100 grams of product in 100 ml of toluene. The amount of this solution needed to give the amount of catalyst shown in the table was used to start a polymerization. Ethylene flowed into the reactor as needed in order to keep the pressure constant at 150 psig as polymer was produced.

At the end of 1 hour (less, if the activity was very high) the ethylene flow was stopped and the reactor was rapidly cooled to room temperature. The reactor was opened and the polymer was filtered from the toluene. The product was dried overnight in a vacuum oven and weighed. The following tables give the reaction conditions and the results of polymerizations.

| Ex | Reactor Rx Temp (°C.) | Time (min) | H2 Amt (mmoles) | Co-monomer | Co-monomer (ml) | Catalyst (mmoles) | Al/Zr (Atomic) | Co-catalyst |
|---|---|---|---|---|---|---|---|---|
| 3 | 80 | 60 | 0 | None | 0 | 9.00E-03 | 1430 | PMAO |
| 4 | 80 | 60 | 0 | None | 0 | 4.50E-03 | 2870 | PMAO |
| 5 | 80 | 60 | 180 | None | 0 | 4.50E-03 | 2870 | PMAO |
| 6 | 80 | 60 | 0 | Butene-1 | 20 | 4.50E-03 | 2870 | PMAO |
| 7 | 110 | 60 | 0 | None | 0 | 4.50E-03 | 2870 | PMAO |
| 8 | 110 | 60 | 0 | None | 0 | 4.50E-03 | 2870 | MAO |
| 9 | 110 | 30 | 30 | None | 0 | 4.50E-03 | 2870 | MAO |
| 10 | 110 | 60 | 0 | Butene-1 | 20 | 4.50E-03 | 2870 | MAO |
| 11 | 110 | 60 | 90 | Butene-1 | 20 | 4.50E-03 | 2870 | MAO |
| 12 | 110 | 30 | 90 | Hexene-1 | 20 | 4.50E-03 | 2870 | MAO |
| 13 | 110 | 60 | 0 | Octene-1 | 20 | 4.50E-03 | 2870 | MAO |
| 14 | 80 | 30 | 30 | Butene-1 | 17 | 4.79E-03 | 1570 | MAO |
| 15 | 80 | 15 | 30 | Butene-1 | 17 | 4.79E-03 | 1570 | MAO |
| 16 | 80 | 30 | 30 | Butene-1 | 17 | 4.79E-03 | 1570 | MAO |
| 17 | 80 | 30 | 30 | Butene-1 | 17 | 4.79E-03 | 2190 | MAO |
| 18 | 110 | 10 | 0 | Butene-1 | 17 | 4.79E-03 | 2190 | MAO |
| 19 | 110 | 30 | 0 | Butene-1 | 17 | 2.87E-03 | 2190 | MAO |
| 20 | 80 | 60 | 0 | 5-vinyl-2-norbornene | 30 | 3.00E-03 | 4500 | MAO |

| Ex. | Wt. PE (g) | Cat Prod (kg/g/hr) | MI2 (dg/min) | MI20 (dg/min) | MFR | Density (g/ml) | Mw/Mn |
|---|---|---|---|---|---|---|---|
| 3 | 77.1 | 93.9 | 0.17 | 2.37 | 13.9 | 0.9574 | 2.00 |
| 4 | 81.3 | 198.1 | 0.14 | 2.57 | 18.0 | 0.9587 | 1.75 |
| 5 | 92.5 | 225.4 | 10.28 | 333 | 32.4 | 0.9720 | — |
| 6 | 71.7 | 174.7 | 1.11 | 24.92 | 22.5 | 0.9323 | — |
| 7 | 70.4 | 171.5 | 1.10 | 22.64 | 20.6 | 0.9616 | 1.70 |
| 8 | 80.1 | 195.2 | 1.50 | 35.81 | 23.9 | 0.9637 | 1.84 |
| 9 | 105.0 | 511.7 | 18.40 | 539 | 29.3 | 0.9714 | 4.194 |
| 10 | 96.5 | 235.1 | 7.92 | 152 | 19.2 | 0.9448 | — |
| 11 | 110.0 | 536.1 | 41.94 | 1202 | 28.7 | 0.9521 | — |
| 12 | 138.9 | 676.9 | 16.27 | 588 | 36.1 | 0.9584 | 4.85 |
| 13 | 65.0 | 158.4 | 9.29 | 185 | 19.9 | 0.9515 | — |
| 14 | 31.8 | 145.7 | 549 | — | — | — | — |
| 15 | 34.5 | 316.1 | <0.01 | 2.89 | — | — | — |
| 16 | 44.5 | 203.8 | 106 | — | — | — | — |
| 17 | 83.6 | 383.0 | 25.8 | 588 | 22.8 | — | — |
| 18 | 66.1 | 908.4 | <0.01 | 49.1 | — | — | — |
| 19 | 33.2 | 253.5 | <0.01 | 31.9 | — | — | — |
| 20 | 49.1 | 179.4 | 0.07 | 1.18 | 17.1 | 0.9415 | — |

The melt index of the polymer was measured according to ASTM D-1238, Condition E and Condition F. MI2 is the melt index measured with a 2.16 kg weight (Condition E). MI20 is the melt index measured with a 21.6 kg weight (Condition F). MFR is the ratio of MI20 to MI2. The polymer density was measured according to ASTM D-1505. The molecular weight distribution of the polymer was measured using a Waters 150C gel permeation chromatograph at 135° C. with 1,2,4-trichlorobenzene as the solvent. Both weight average molecular weight ($M_w$) and ratio of $M_w$ to $M_n$ (number average molecular weight) are used to characterize the molecular weight distribution. The table shows a high activity at 80° C. and little or no decline in activity at 110° C. (Examples 9 vs. 2).

The catalyst has excellent comonomer incorporation properties. Note the unusually high butene-1 incorporation in Examples 6 and 10 which produced relatively low polymer densities. In addition, the catalyst readily incorporates comonomers which are usually difficult to copolymerize. This is exemplified by the copolymerization of ethylene and 5-vinyl-2-norbornene in Example 20. In Example 3, the ratio of the weight average molecular weight to the number average molecular weight, which is an indication of the molecular weight distribution, was measured as 2.00. An Mw/Mn of 2.00 indicates a very narrow molecular weight distribution.

We claim:

1. A method of polymerizing an α-olefin comprising heating said α-olefin in the presence of a catalyst having the general formula $$\left[ \begin{array}{c} X \\ | \\ Q-M-L \\ | \\ X \end{array} \right] \cdot B_L$$

where Q is a ligand containing the ring

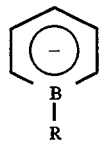

R is selected from the group consisting of hydrogen, $N(R')_2$, $OR'$, and $R'$, each $R'$ is independently selected from the group consisting of alkyl from $C_1$ to $C_{10}$, aryl from $C_6$ to $C_{15}$, alkaryl from $C_7$ to $C_{15}$, and aralkyl from $C_7$ to $C_{15}$, each X is independently selected from the group consisting of hydrogen, halogen, alkoxy from $C_1$ to $C_{10}$, dialkylamino from $C_1$ to $C_{10}$, methyl,

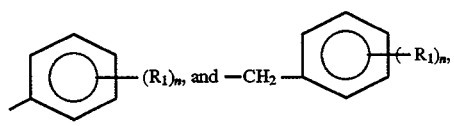

each $R_1$ is independently selected from the group consisting of halogen, alkoxy from $C_1$ to $C_{10}$, and $R'$, L is selected from the group consisting of

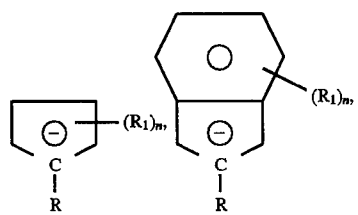

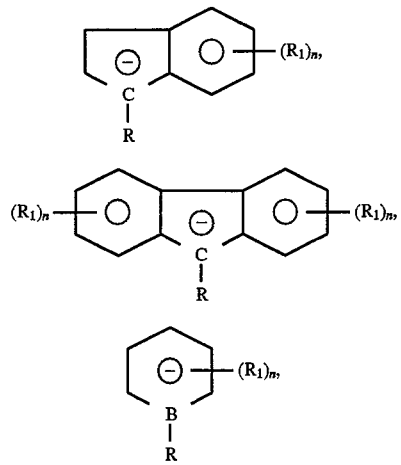

Q, and X, where L can be bridged to Q, $B_L$ is an optional Lewis base, "n" is 0 to 5, and M is selected from the group consisting of titanium, zirconium, and hafnium.

2. The method of claim 1 wherein said α-olefin is further heated in the presence of an organometallic co-catalyst.

3. The method of claim 2 wherein the co-catalyst is either methylalumoxane or polymethylalumoxane or an aluminum alkyl of the formula $AlR'_x(R_2)_{3-x}$, wherein R' is selected from the group consisting of a $C_1$ to $C_{10}$ alkyl, $C_6$ to $C_{15}$ aryl, a $C_7$ to $C_{15}$ alkaryl, and a $C_7$ to $C_{15}$ aralkyl, $1 \leq x \leq 3$, and $R_2$ is hydrogen, halide, or a $C_1$ to $C_{20}$ alkyl or alkoxide group.

4. The method of claim 3 wherein the co-catalyst is triethylaluminum or ethylaluminum dichloride.

5. The method of claim 3 wherein the co-catalyst is methylalumoxane or polymethylalumoxane.

6. The method of claim 2 wherein the α-olefin is polymerized in a solvent in which both the catalyst and co-catalyst are soluble.

7. The method of claim 5 wherein the α-olefin is polymerized in a solvent in which both the catalyst and co-catalyst are soluble.

8. The method of claim 7 wherein the solvent is toluene, xylene, benzene, or ethylbenzene.

9. The method of claim 2 wherein the mole ratio of the organometallic co-catalyst to catalyst is about 0.01:1 to about 100,000:1.

10. The method of claim 9 wherein the mole ratio of the organometallic co-catalyst to catalyst is about 1:1 to about 10,000:1.

11. The method of claim 1 wherein the α-olefin is further polymerized in the presence of an acid salt that contains a non-coordinating inert anion.

12. The method of claim 11 wherein the acid salt is a non-nucleophilic compound consisting of bulky ligands attached to a boron or aluminum atom.

13. The method of claim 12 wherein the acid salt is lithium tetrakis(pentafluorophenyl)borate, lithium tetrakis (pentafluorophenyl)aluminate, anilinium tetrakis (pentafluorophenyl)borate, or a mixture thereof.

14. The method of claim 11 wherein the mole ratio of acid salt to catalyst is about 0.01:1 to about 1000:1.

15. The method of claim 14 wherein the mole ratio of acid salt to catalyst is about 1:1 to about 10:1.

16. The method of claim 1 wherein the α-olefin is ethylene.

17. The method of claim 1 wherein the α-olefin is a mixture of ethylene and at least one ethylenically unsaturated monomer.

18. The method of claim 17 wherein the ethylenically unsaturated monomer is selected from the group consisting of propylene, 1-butylene, 1-hexene, 1-octene, 1,3-butadiene, 1,4-hexadiene, 1,5-hexadiene, norbornene, ethylidene norbornene and vinyl norbornene.

19. The method of claim 1 wherein each X is chlorine or a methyl group.

20. The method of claim 1 wherein L is cyclopentadienyl or chlorine.

21. The method of claim 1 wherein Q is

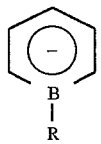

and R is —N(R')$_2$ or phenyl.

22. The method of claim 1 wherein Q is selected from the group consisting of

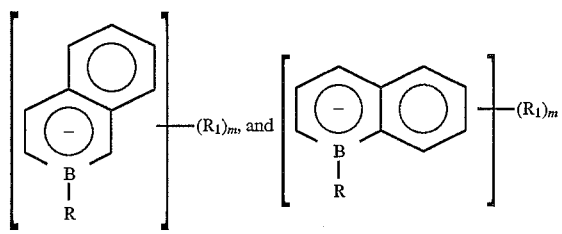

wherein "m" is 0 to 7, or

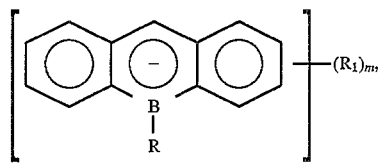

wherein "m" is 0 to 9.

23. A method of polymerizing an ethylenically unsaturated monomer which comprises heating said ethylenically unsaturated monomer in the presence of a catalyst of the general formula

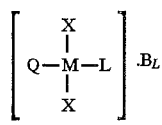

where Q is a ligand containing the ring

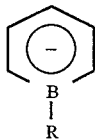

R is selected from the group consisting of hydrogen, N(R')$_2$, OR', and R', each R' is independently selected from the group consisting of alkyl from $C_1$ to $C_{10}$, aryl from $C_6$ to $C_{15}$, alkaryl from $C_7$ to $C_{15}$, and aralkyl from $C_7$ to $C_{15}$, each X is independently selected from the group consisting of hydrogen, halogen, alkoxy from $C_1$ to $C_{10}$, dialkylamino from $C_1$ to $C_{10}$, methyl,

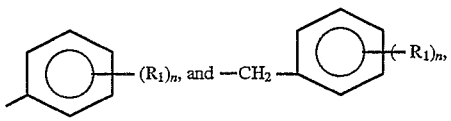

each R$_1$ is independently selected from the group consisting of halogen, alkoxy from $C_1$ to $C_{10}$, and R', L is selected from the group consisting of

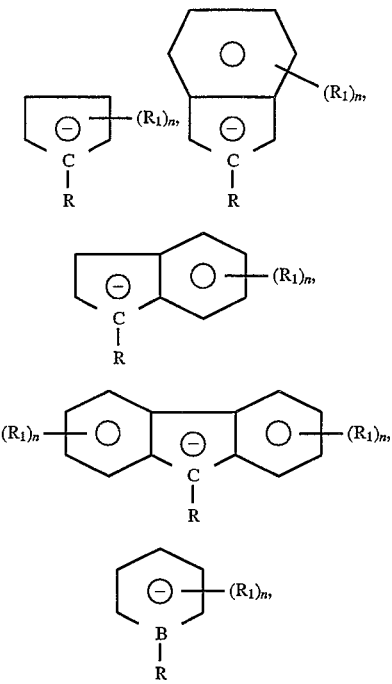

Q, and X, where L can be bridged to Q, B$_L$ is an optional Lewis base, "n" is 0 to 5, and M is selected from the group consisting of titanium, zirconium, and hafnium.

24. A method of polymerizing monomer that comprises ethylene or a mixture of ethylene and a monomer copolymerizable therewith comprising heating said monomer in the presence of a catalyst having the general formula

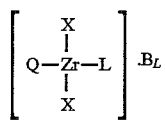

where Q is bora-benzene, bora-naphthalene, or bora-anthracene, or phenyl, each X is independently selected from chlorine or methyl, L is Q, cyclopentadienyl, or chlorine, where L can be bridged to Q, and B$_L$ is an optional Lewis base.

25. The method of claim 24 wherein said catalyst comprises β-dimethylaminoborobenzene cyclopentadienylzirconium dichloride or cyclopentadienyl (9-mesitylboraanthracenyl) zirconium dichloride.

* * * * *